United States Patent
Song et al.

(10) Patent No.: US 10,351,859 B2
(45) Date of Patent: Jul. 16, 2019

(54) MICROORGANISM PRODUCING L-LEUCINE AND METHOD FOR PRODUCING L-LEUCINE USING THE SAME

(71) Applicant: CJ Cheiljedang Corporation, Seoul (KR)

(72) Inventors: Byeong Cheol Song, Gyeonggi-do (KR); Ji Hye Lee, Gyeonggi-do (KR); Ae Ji Jeon, Seoul (KR); Jong Hyun Kim, Gyeonggi-do (KR); Hye Won Kim, Gyeonggi-do (KR)

(73) Assignee: CJ Cheiljedang Corporation, Seoul (KR)

(*) Notice: Subject to any disclaimer, the term of this patent is extended or adjusted under 35 U.S.C. 154(b) by 0 days.

(21) Appl. No.: 15/754,903

(22) PCT Filed: Aug. 25, 2016

(86) PCT No.: PCT/KR2016/009438
§ 371 (c)(1),
(2) Date: Feb. 23, 2018

(87) PCT Pub. No.: WO2017/034343
PCT Pub. Date: Mar. 2, 2017

(65) Prior Publication Data
US 2018/0251772 A1    Sep. 6, 2018

(30) Foreign Application Priority Data

Aug. 25, 2015 (KR) .................. 10-2015-0119785

(51) Int. Cl.
*C12P 13/06* (2006.01)
*C12N 15/77* (2006.01)
*C12R 1/15* (2006.01)

(52) U.S. Cl.
CPC .............. *C12N 15/77* (2013.01); *C12P 13/06* (2013.01); *C12R 1/15* (2013.01)

(58) Field of Classification Search
None
See application file for complete search history.

(56) References Cited

U.S. PATENT DOCUMENTS

| 3,865,690 | A | 2/1975 | Okumura et al. |
| 5,763,231 | A | 6/1998 | Ono et al. |
| 2018/0251772 | A1* | 9/2018 | Song ............ C12N 15/77 |

FOREIGN PATENT DOCUMENTS

| CN | 103031265 B | 4/2014 |
| JP | S4824275 B1 | 7/1973 |
| KR | 10-0438146 B1 | 8/1998 |
| KR | 10-1998-0082891 A | 12/1998 |
| KR | 10-0220018 B1 | 1/1999 |
| KR | 10-1998-0039740 | 11/2004 |

OTHER PUBLICATIONS

Manual of Methods for General Bacteriology. 1981. Washington D.C.: American Society for Bacteriology (excerpt—6 pages).
International Search Report dated Dec. 16, 2016 for International Application No. PCT/KR2016/009438 filed Aug. 25, 2016, 5 pages.
Written Opinion dated Dec. 16, 2016 for International Application No. PCT/KR2016/009438 filed Aug. 25, 2016, 5 pages.
Office Action issued in Japanese Patent Application No. 2018-510395, dated Jan. 22, 2019.

* cited by examiner

*Primary Examiner* — Hope A Robinson
(74) *Attorney, Agent, or Firm* — Knobbe Martens Olson & Bear LLP

(57) ABSTRACT

The present disclosure relates to a microorganism producing L-leucine and a method for producing L-leucine using the same, and more specifically, to a *Corynebacterium glutamicum* mutant which has resistance to L-leucine and a derivative thereof and improved L-leucine producing ability, and a method for producing L-leucine using the same.

4 Claims, 3 Drawing Sheets

MICROORGANISM PRODUCING L-LEUCINE AND METHOD FOR PRODUCING L-LEUCINE USING THE SAME

CROSS-REFERENCE TO RELATED APPLICATIONS

This application is a U.S. National Phase Application of PCT International Application No. PCT/KR2016/009438, filed on Aug. 25, 2016 and published as WO 2017/034343 A1 on Mar. 2, 2017, designating the United States of America, which is an International Application of and claims the benefit of priority to Korean Patent Application No. 10-2015-0119785, filed on Aug. 25, 2015.

TECHNICAL FIELD

The present disclosure relates to a microorganism producing L-leucine and a method for producing L-leucine using the microorganism.

BACKGROUND ART

Branched-chain amino acids refer to three kinds of amino acids (i.e., L-valine, L-leucine, and L-isoleucine) and they are known to be mainly metabolized in the muscle and used as an energy source during physical activity. Along with the increased awareness with respect to the important roles of these branched-chain amino acids in maintaining and increasing muscle mass during physical activity, their use is also on the rise. In particular, L-leucine is an essential amino acid and is widely used in medicines, foods, feed additives, industrial chemicals, etc.

Meanwhile, these branched-chain amino acids are mainly produced by microorganisms of the genus *Escherichia* or the genus *Corynebacterium*, and are known to be biosynthesized from 2-ketoisocaproic acid, a precursor, after undergoing several steps from pyruvic acid (Korean Patent Nos. 10-0220018 and 10-0438146). However, the enzymes involved in the leucine biosynthesis have a problem in that they undergo feedback inhibition caused by the final product, i.e., L-leucine or a derivative thereof, thus making it difficult to perform large-scale industrial production of L-leucine.

DISCLOSURE

Technical Problem

The inventors of the present disclosure have made efforts to develop microorganisms producing L-leucine in a higher yield compared to conventional strains. As a result, they have discovered that mutants obtained using a glutamic acid-producing microorganism have resistance to norleucine (NL) (i.e., a leucine derivative), and that the feedback inhibition by L-leucine or a derivative thereof is released in these mutants, and thus L-leucine is produced in high yield, thereby completing the present disclosure.

Technical Solution

An object of the present disclosure is to provide a *Corynebacterium glutamicum* mutant having novel L-leucine producing ability.

Another object of the present disclosure is to provide a method for producing L-leucine using the *Corynebacterium glutamicum* mutant.

Advantageous Effects of the Invention

The microorganism of the genus *Corynebacterium glutamicum* is a microorganism having resistance to L-leucine or a derivative thereof and can thus prevent feedback inhibition and have improved L-leucine productivity compared to its parent strain. Accordingly, the method for producing L-leucine using the microorganism of the present disclosure can produce L-leucine in high efficiency and high yield.

BEST MODE

An aspect of the present disclosure provides a novel *Corynebacterium glutamicum* mutant (modified *Corynebacterium glutamicum* strain) producing L-leucine, and specifically, a mutant deposited under Accession No. KCCM11661P and a mutant deposited under Accession No. KCCM11662P for producing L-leucine.

As used herein, the term "L-leucine", which is an essential amino acid, refers to an L-amino acid represented by the formula $HO_2CCH(NH_2)CH_2CH(CH_3)_2$ that structurally corresponds to branched-chain amino acids along with L-valine and L-isoleucine.

Figure 1:
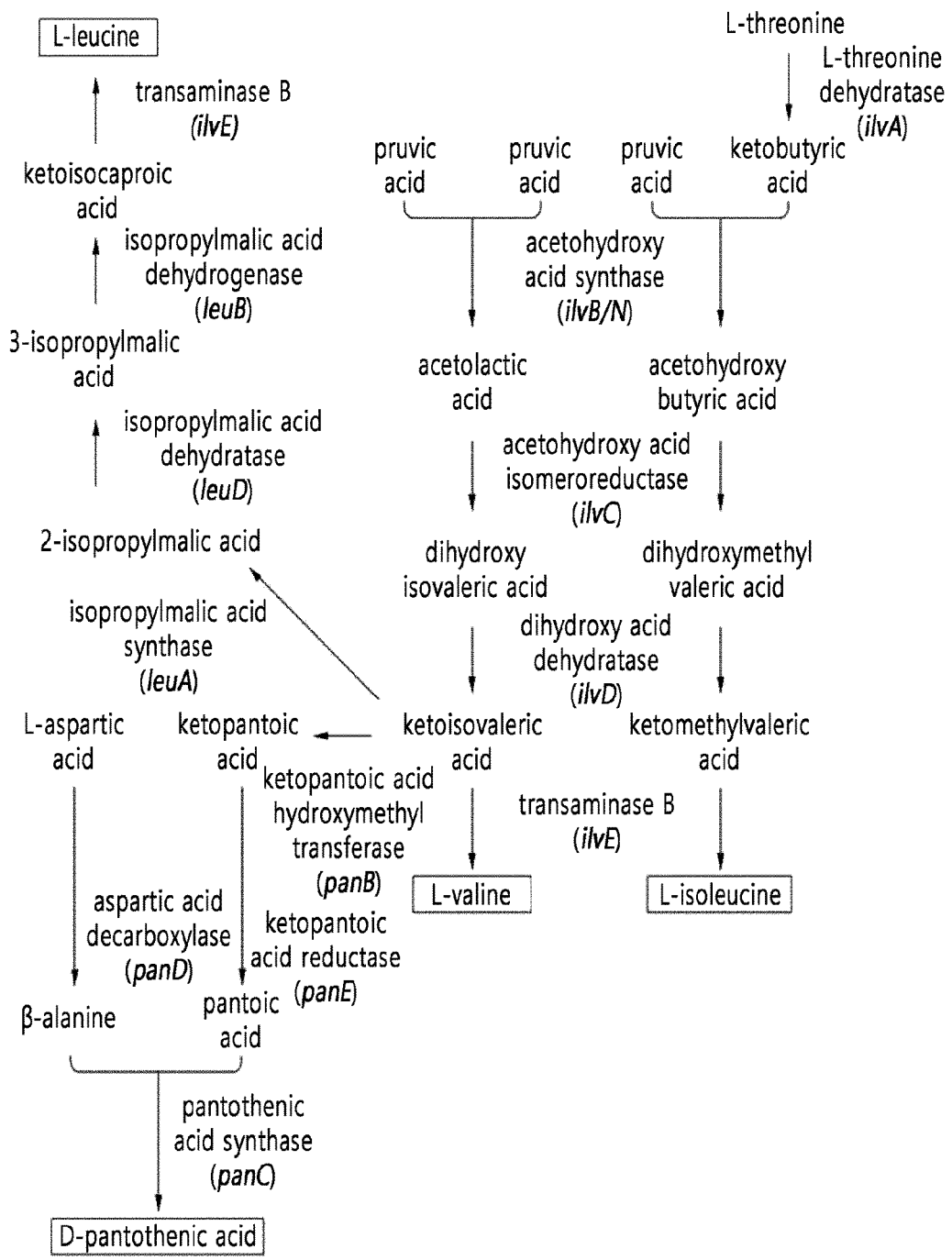
FIG. 1 is a flowchart illustrating a biosynthetic pathway of L-leucine, which is the final product of the present disclosure.
Figure 2:
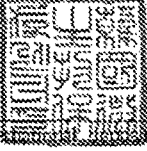
FIG. 2 is a copy of the deposit receipt of the *Corynebacterium glutamicum* strain named KCJ-24, deposited under Budapest Treaty on Jan. 22, 2015 at the Korean Culture Center of Microorganisms, and assigned Accession Number KCCM11661P.
Figure 3:
FIG. 3 is a copy of the deposit receipt of the *Corynebacterium glutamicum* strain named KCJ-28, deposited under Budapest Treaty on Jan. 22, 2015 at the Korean Culture Center of Microorganisms, and assigned Accession Number KCCM11662P.

Meanwhile, with respect to the biosynthesis of L-leucine in microorganisms, it is known that L-leucine is biosynthesized from pyruvic acid via acetolactic acid, dihydroxy isovaleric acid, ketoisovaleric acid, 2-isopropylmalic acid, 3-isopropylmalic acid, and ketoisocaproic acid through the biosynthetic process shown in FIG. 1. Additionally, L-leucine is biosynthesized by catalyzing the biosynthetic process using enzymes, such as acetohydroxy acid synthase, acetohydroxy acid isomeroreductase, dihydroxy acid dehydratase, isopropylmalic acid synthase, isopropylmalic acid dehydratase, isopropylmalic acid dehydrogenase, and transaminase B. However, it is difficult to industrially produce only one type of branched-chain amino acid through fermentation because the enzymes used in the pathways are the same in the biosynthetic process of branched-chain amino acids (i.e., L-valine, L-isoleucine, and L-leucine). Additionally, due to the occurrence of feedback inhibition by the final product (i.e., L-leucine or a derivative thereof), there has been a problem in the industrial, large-scale production of L-leucine. In this regard, the mutant of the present disclosure can have resistance to L-leucine or a derivative thereof.

As used herein, the term "derivative" may refer to compounds which are known to be capable of inhibiting the L-leucine producing ability of microorganisms by inducing feedback inhibition in relation to the biosynthesis of L-leucine, the final product of the present disclosure. Examples of the compounds may include isoleucine, terleucine, norleucine, cycloleucine, etc., but are not limited thereto. Specifically, the mutant may have resistance to at least one material selected from the group consisting of leucine, isoleucine, terleucine, norleucine, and cycloleucine, and more specifically, to norleucine. Generally, it is known that L-leucine biosynthesis is inhibited when L-leucine is accumulated above a certain level in a cell. Therefore, any strain having resistance to the derivative can release the inhibition by L-leucine and can produce L-leucine even at a high L-leucine concentration.

A desired mutant of the microorganism producing L-leucine of the present disclosure may be obtained by mutagenesis of its parent strain. In particular, mutagenesis of the microorganism may be performed by various methods well known in the art, and either physical or chemical mutagenesis may be used. For example, examples of chemical mutagens suitable for the present disclosure may include N-methyl-N'-nitro-N-nitrosoguanidine (NTG), diepoxybutane, ethyl methanesulfonate, mustard compounds, hydrazine, and nitrite, but the chemical mutagens are not limited thereto. Additionally, examples of physical mutagens may include ultraviolet and gamma radiations, but the physical mutagens are not limited thereto.

When mutagenesis is induced, a parent strain is affected by a mutagen at a concentration that can leave a particular size of a surviving population of the parent strain. The size varies with the type of the mutagen and depends on the amount of mutation being induced within the surviving population at a constant killing rate. For example, in the case of NTG, the killing rate can leave approximately 10% to 50% of the starting population viable. Mutagenesis by nitrous acid can leave approximately 0.01% to 0.1% of the starting population viable, and mutagenesis by ultraviolet light can leave approximately 1.0% of the starting population viable, but the mutagens are not limited thereto.

Another aspect of the present disclosure provides a method for producing L-leucine which includes culturing a *Corynebacterium glutamicum* mutant and recovering L-leucine from the *Corynebacterium glutamicum* mutant or a culture thereof.

As used herein, the term "culturing" means that microorganisms are grown in appropriately, artificially controlled environmental conditions. The culturing of the microorganism of the present disclosure may be performed using the method for culturing *Corynebacterium glutamicum* widely known in the art. Specifically, examples of the culturing methods may include a batch culture, a continuous culture, and a fed-batch culture, but the culturing methods are not limited thereto. These various methods are disclosed, for example, in "Biochemical Engineering" (James M. Lee, Prentice-Hall International Editions, pp. 138 to 176, 1991), etc.

As used herein, the term "culture" refers to a material containing a medium in which a microorganism is being grown or has grown in appropriately, artificially controlled environmental conditions. The culture does not include a grown microorganism in a narrow sense, but may include it in a broad sense. The "culture" includes various materials which were released into the medium by a microorganism during its growth together with the medium components constituted for culturing the microorganism, and specifically, leucine, which is the target material.

The medium used for the cultivation must meet the requirements for the cultivation of a specific strain in an appropriate manner Examples of the culture media for *Corynebacterium* strains are disclosed (e.g., *Manual of Methods for General Bacteriology*. American Society for Bacteriology. Wash. D.C., U.S.A., 1981). Examples of carbon sources to be used may include saccharides and carbohydrates, such as glucose, saccharose, lactose, fructose, maltose, starch, and cellulose; oils and fats, such as soy bean oil, sunflower oil, castor oil, and coconut oil; fatty acids, such as palmitic acid, stearic acid, and linoleic acid; alcohols, such as glycerol and ethanol; and organic acids, such as acetic acid, but the carbon sources are not limited thereto. These materials may be used alone or in combination. Examples of nitrogen sources to be used may include peptone, yeast extract, meat extract, malt extract, corn steep liquor, soy bean flour, and urea; or inorganic compounds, such as ammonium sulfate, ammonium chloride, ammonium phosphate, ammonium carbonate, and ammonium nitrate, but the nitrogen sources are not limited thereto. The nitrogen sources may be used alone or in combination. Examples of phosphorus sources to be used may include potassium dihydrogen phosphate or dipotassium hydrogen phosphate or corresponding sodium-containing salts thereof, but the phosphorus sources are not limited thereto. Additionally, the culture media may include metal salts such as magnesium sulfate and ferric sulfate that are necessary for growth. In addition to the above substances, essential growth materials, such as amino acids and vitamins, may be included. Appropriate precursors may also be used in the culture media. The above-mentioned materials may be added to the culture media in an appropriate manner by batch culture or continuous culture during cultivation.

Meanwhile, the pH of the culture may be adjusted using basic compounds such as sodium hydroxide, potassium hydroxide, and ammonia, or acid compounds such as phosphoric acid and sulfuric acid, in an appropriate manner. Additionally, the generation of air bubbles may be prevented using an antifoaming agent such as fatty acid polyglycol ester. To maintain aerobic conditions, oxygen or an oxygen-containing gas (e.g., air) is injected into the culture. Generally, the temperature of the culture media may be in a range of 20° C. to 45° C. The cultivation is continued until the L-leucine production reaches its maximum level, which is normally achieved in from 10 to 160 hours. L-Leucine may be released into the culture media or contained within the cells.

The method for recovering L-leucine from the cells or culture media may be performed by a conventional method known in the art, for example, centrifugation, filtration, anion exchange chromatography, crystallization, HPLC, etc., but the method is not limited thereto.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

Example 1: Selection of Mutants by Artificial Mutagenesis

To obtain microorganism mutants producing L-leucine, modification of a microorganism was induced by the following method.

Specifically, parent strains (i.e., glutamic acid-producing *Corynebacterium glutamicum* ATCC 14067 and *Corynebacterium glutamicum* ATCC 13869), which were activated by culturing in an activation medium for 16 hours, were inoculated into a seed medium that was sterilized at 121° C. for 15 minutes, and cultured therein for 14 hours. Then, 5 mL of the culture medium was collected and washed with 100 mM citrate buffer, and N-methyl-N'-nitro-N-nitrosoguanidine (NTG) was added thereto to a final concentration of 200 mg/L. After treating for 20 minutes, the culture medium was washed with 100 mM phosphate buffer. The strains treated with NTG were spread on a minimal medium and the death rate was measured. As a result, the death rate was confirmed to be 85%. In order to select modified strains having resistance to norleucine (NL), which corresponds to a derivative of L-leucine, the NTG-treated strains were spread on a minimal medium containing NL at a final concentration of 20 mM, 30 mM, 40 mM, and 50 mM, respectively. Then, the strains were cultured at 30° C. for 5 days, and thereby mutants having resistance to NL were obtained.

The mutants thus obtained were designated as *Corynebacterium glutamicum* KCJ-24 and *Corynebacterium glutamicum* KCJ-28, respectively, and were deposited at the Korean Culture Center of Microorganisms (KCCM), Yurim B/D, 45, Hongjenae-2ga-gil, Seodaemun-gu, Seoul 120-861, Republic of Korea, which is an international depositary authority under the Budapest Treaty, on Jan. 22, 2015, and assigned Accession Nos. KCCM11661P and KCCM11662P, respectively. During the pendency of this application, access to the invention will be afforded to the Commissioner upon request. All restrictions upon availability to the public will be irrevocably removed upon granting of the patent. The deposits will be maintained in a public depository for a period of 30 years or 5 years after the last request or for the effective life of the patent whichever is longer. The deposits were viable at the time of deposit. The deposits will be replaced if they become non-viable.

The compositions of the culture media used in Examples 1 and 2 are as follows:

Activation Medium

Beef extract 1%, Polypeptone 1%, Sodium Chloride 0.5%, Yeast Extract 1%, Agar 2%, pH 7.2

Seed Medium

Glucose 5%, Bacto Peptone 1%, Sodium Chloride 0.25%, Yeast Extract 1%, Urea 0.4%, pH 7.2

Minimal Medium

Glucose 1.0%, Ammonium Sulfate 0.4%, Magnesium Sulfate 0.04%, Potassium Dihydrogen Phosphate 0.1%, Urea 0.1%, Thiamine 0.001%, Biotin 200 μg/L, Agar 2%, pH 7.0

Example 2: Examination of L-Leucine Producing Ability of Mutants

*Corynebacterium glutamicum* KCJ-24 and *Corynebacterium glutamicum* KCJ-28, which were obtained in Example 1 and were confirmed to have resistance to NL at high concentrations, were cultured by the following method, so as to confirm their L-leucine producing ability.

*Corynebacterium glutamicum* ATCC 14067 and *Corynebacterium glutamicum* ATCC 13869 (i.e., parent strains), and the two mutants were each inoculated into 250 mL corner baffle flasks containing 25 mL of the seed medium below, and cultured at 30° C. for 20 hours with shaking at 200 rpm to obtain seed culture media. Thereafter, 1 mL of each of the seed culture media was inoculated into a 250 mL corner baffle flask containing 24 mL of the following production medium, and cultured at 30° C. for 72 hours with shaking at 200 rpm to produce L-leucine.

The composition of the production medium used in the present Example 2 is as follows.

Production Medium

Glucose 5%, Ammonium Sulfate 2%, Potassium Dihydrogen Phosphate 0.1%, Magnesium Sulfate Heptahydrate 0.05%, Corn Steep Liquor (CSL) 2.0%, Biotin 200 μg/L, pH 7.2

Upon completion of cultivation, the amount of L-leucine production was measured by high-performance liquid chromatography (HPLC). The concentrations of L-leucine in the culture media for each strain for experiments are summarized in Table 1 below.

TABLE 1

Comparison of L-leucine producing ability between *Corynebacterium glutamicum* KCJ-24 and *Corynebacterium glutamicum* KCJ-28

|  | *Corynebacterium glutamicum* ATCC 14067 (Parent Strain) | *Corynebacterium glutamicum* KCJ-24 (Modified Strain) | *Corynebacterium glutamicum* ATCC 13869 (Parent Strain) | *Corynebacterium glutamicum* KCJ-28 (Modified Strain) |
|---|---|---|---|---|
| L-Leucine Conc. (g/L) | 0.1 | 2.7 | 0.3 | 3.1 |

As a result, as shown in Table 1, the parent strains (i.e., *Corynebacterium glutamicum* ATCC 14067 and *Corynebacterium glutamicum* ATCC 13869) produced 0.1 g/L and 0.3 g/L of L-leucine, respectively, but the mutants (i.e., *Corynebacterium glutamicum* KCJ-24 and *Corynebacterium glutamicum* KCJ-28) according to the present disclosure produced 2.7 g/L and 3.1 g/L of L-leucine, respectively, confirming that the L-leucine producing ability of the mutants increased by at least about 10 times compared to those of the parent strains.

The above results suggest that the mutants having resistance to L-leucine and norleucine are not affected by feedback inhibition by leucine or a derivative thereof and thus can produce L-leucine in high efficiency and high yield.

What is claimed is:

1. A *Corynebacterium glutamicum* mutant that produces L-leucine selected from the group consisting of a mutant deposited under Accession No. KCCM11661P and a mutant deposited under Accession No. KCCM11662P.

2. The *Corynebacterium glutamicum* mutant of claim 1, wherein the mutant has resistance to L-leucine and a derivative thereof,
and wherein the derivative is selected from the group consisting of leucine, isoleucine, terleucine, norleucine, and cycloleucine.

3. The *Corynebacterium glutamicum* mutant of claim 2, wherein the L-leucine derivative is norleucine (NL).

4. A method for producing L-leucine, comprising:
culturing the *Corynebacterium glutamicum* mutant of claim 1; and recovering L-leucine from the *Corynebacterium glutamicum* mutant or the culture.

\* \* \* \* \*